(12) United States Patent  
Mersch

(10) Patent No.: US 6,361,530 B1
(45) Date of Patent: Mar. 26, 2002

(54) DURABLE FIBER OPTIC DIFFUSER TIP AND METHOD OF MAKING SAME

(75) Inventor: Steven H. Mersch, Germantown, OH (US)

(73) Assignee: Indigo Medical Incorporated

( * ) Notice: Subject to any disclaimer, the term of this patent is extended or adjusted under 35 U.S.C. 154(b) by 0 days.

(21) Appl. No.: 09/532,893

(22) Filed: Mar. 22, 2000

(51) Int. Cl.⁷ ................................................ A61B 18/18
(52) U.S. Cl. .......................... 606/16; 606/13; 606/15; 264/1.24; 264/1.25; 385/15; 385/123; 385/128; 385/141
(58) Field of Search .................... 606/2, 10, 13–17, 606/167; 607/88, 89; 264/1.1, 1.24, 1.25; 385/15, 24, 31, 123–128, 141

(56) References Cited

U.S. PATENT DOCUMENTS

| | | | |
|---|---|---|---|
| 4,420,796 A | 12/1983 | Mori | 362/32 |
| 4,660,925 A | 4/1987 | McCaughan, Jr. | 350/96.15 |
| 4,693,556 A | 9/1987 | McCaughan, Jr. | 350/320 |
| 4,878,492 A | 11/1989 | Sinofsky et al. | 128/303.1 |
| 5,074,632 A | 12/1991 | Potter | 385/31 |
| 5,151,096 A | 9/1992 | Khoury | 606/15 |
| 5,196,005 A | 3/1993 | Doiron et al. | 606/7 |
| 5,207,669 A | 5/1993 | Baker et al. | 606/7 |
| 5,239,026 A | 8/1993 | Babirad et al. | 526/245 |
| 5,269,777 A | 12/1993 | Doiron et al. | 606/7 |
| 5,330,465 A * | 7/1994 | Doiron et al. | 606/7 |
| 5,333,234 A | 7/1994 | Hashimoto et al. | 385/145 |
| 5,352,712 A | 10/1994 | Shustack | 522/31 |
| 5,431,647 A * | 7/1995 | Purcell, Jr. et al. | 606/16 |
| 5,534,000 A | 7/1996 | Bruce | 606/15 |
| 5,536,265 A * | 7/1996 | Van Den Bergh et al. | 606/2 |
| 5,690,863 A | 11/1997 | Schuman | 252/582 |
| 5,695,583 A | 12/1997 | van den Bergh et al. | 156/153 |
| 5,754,717 A | 5/1998 | Esch | 385/31 |
| 5,814,041 A | 9/1998 | Anderson et al. | 606/15 |
| 5,868,734 A * | 2/1999 | Soufiane et al. | 606/15 |
| 5,951,920 A | 9/1999 | Schuman et al. | 252/582 |

* cited by examiner

*Primary Examiner*—Linda C. M. Dvorak
*Assistant Examiner*—Ahmed Farah

(57) ABSTRACT

An medical instrument for diffusing light from an optical fiber is provided. The medical instrument includes an optical fiber having a proximal portion including a cladding layer surrounding the core and a distal portion having a diffuser tip comprising a protective coating made of acrylic or methylpentene surrounding the core, an optical coupling layer, and a sleeve. The protective coating strengthens the distal end of the optical fiber so that it can withstand a higher bending moment at failure than the uncladded core. At the same time, the protective layer has an index of refraction that is between the indices of refraction of the core and the optical coupling layer to direct light out of the core through to the optical coupling layer.

8 Claims, 2 Drawing Sheets

DURABLE FIBER OPTIC DIFFUSER TIP AND METHOD OF MAKING SAME

FIELD OF THE INVENTION

The present invention relates, in general, to an improved, more durable diffuser tip to diffuse light from a light-emitting end of an optical fiber. More particularly, the invention relates to a diffuser which includes a decladded optical fiber core which is covered by a protective coating and an optical coupling layer wherein the protective coating has an index of refraction between the indices of refraction of the core and the optical coupling layer while at the same time the protective coating increases the bending moment required to break the core. The protective coating is made of polymethyl methacrylate or methylpentene.

BACKGROUND OF THE INVENTION

Surgeons commonly use lasers to treat benign prostatic hyperplasia, or BPH. BPH is a condition of an enlarged prostate gland. The prostate gland with BPH typically increases in size to between about two and four times normal. The lasers used to treat it must have durable diffuser tips that distribute light radially in a predictable manner and bend without breaking. Small diffuser tips offer an advantage to the surgeon as well. Builders of these diffuser tips commonly make them from optical fibers and desire to make them small.

An optical fiber typically contains a glass core surrounded by cladding and a jacket. The cladding protects the inherently weaker glass core by lending mechanical support to the core. The cladding also has an index of refraction lower than that of the core to block light from emerging radially from the core.

A prior art diffuser tip based on art taught by Esch in U.S. Pat. No. 5,754,717is shown in FIG. 1. This figure shows a prior art diffuser tip comprised of the stripped core of a typical optical fiber, an optical coupling layer, and a sleeve. The optical coupling layer, replacing the cladding of the optical fiber, has an index of refraction exceeding that of the core to pull the light out of the core using well known physical principles. The sleeve, which surrounds the optical coupling layer, has an index of refraction lower than the optical coupling layer and includes barium sulfate particles to help scatter the light. In order to allow light to pass through the boundary between the optical coupling layer and the sleeve, the inner diameter of the sleeve is abraded. Abrading the surface of the sleeve presents surfaces more nearly normal to the light coming through the optical coupling layer so that the light passes into the sleeve. By controlling the extent of the abrasions, the light intensity as a function of the position along the axis of the sleeve can also be controlled. Designers often prefer an even distribution of light for applications involving BPH.

A diffuser tip taught by Khoury in U.S. Pat. No. 5,151,096comprises a layer of medical grade epoxy over the core. Medical grade epoxy has an index of refraction higher than that of silicone and so cannot be used in an application having a silicone optical coupling layer.

The process of making the diffuser tip illustrated in FIG. 1 involves stripping a portion of the optical fiber cladding layer away from the optical fiber core. The sleeve is then filled with an appropriate material such as silicone and the declad portion of the core is inserted into the sleeve. Since the cladding layer provides structural support for the core, stripping it away makes the declad portion of the optical fiber core more susceptible to cracking or breaking when it is bent. The problem of cracking or breaking becomes more acute as the diameter of the optical fiber core becomes smaller. While the optical coupling layer and sleeve protect the declad portion of the optical fiber core, the support provided is not as great as the support provided by the cladding layer. It would, therefore, be advantageous to design a diffuser tip wherein the resistance of the declad core to cracking or breaking is improved. It would further be advantageous to design a more resilient diffuser tip without substantially changing the light emitting properties of current designs.

SUMMARY OF THE INVENTION

One embodiment of the present invention includes a diffuser tip fashioned from an optical cable's stripped glass core surrounded by a durable protective coating of acrylic and an optical coupling layer. A Teflon sleeve impregnated with barium sulfate covers the optical coupling layer. The optical coupling layer transfers the light from the protective coating through to the sleeve. The index of refraction of the protective coating exceeds that of the core to couple light from the core by well-known physical principles. The index of refraction of the optical coupling layer exceeds that of the protective coating to couple the light from the protective coating to the sleeve. The material of the protective coating, by enhancing the strength of the declad core while effectively coupling light out of the core to the optical coupling layer, results in an operative diffuser tip that increases the bending moment at which the declad core breaks. In a particular embodiment of the invention the coating comprises polymethyl methacrylate. In a further embodiment of the invention the coating comprises methylpentene.

In a further embodiment of the invention the inner surface of the sleeve is abraded to couple light from the optical coupling layer into the sleeve. The sleeve's index of refraction is lower than the index of refraction of the optical coupling layer. The abrasion scatters the light rays to allow them to pass into the sleeve when the light rays travel from a layer of higher refractive index to a layer of lower refractive index.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
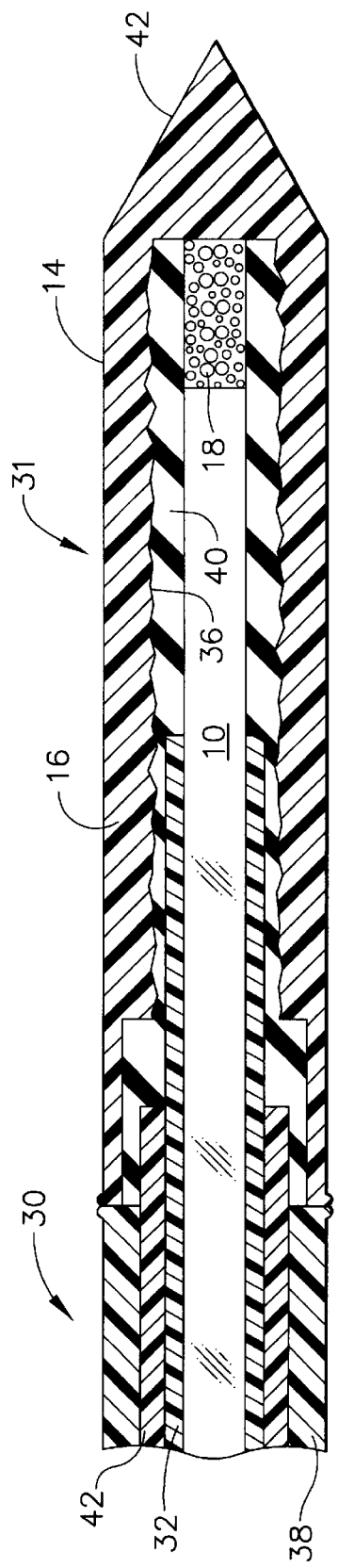
FIG. 1 is a section view of a prior art diffuser tip.
Figure 2:
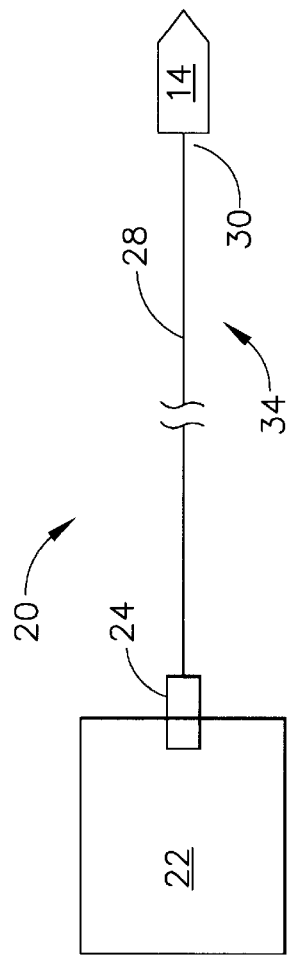
FIG. 2 is a diagram view of a laser device utilizing the diffuser tip assembly according to the present invention.
Figure 3:
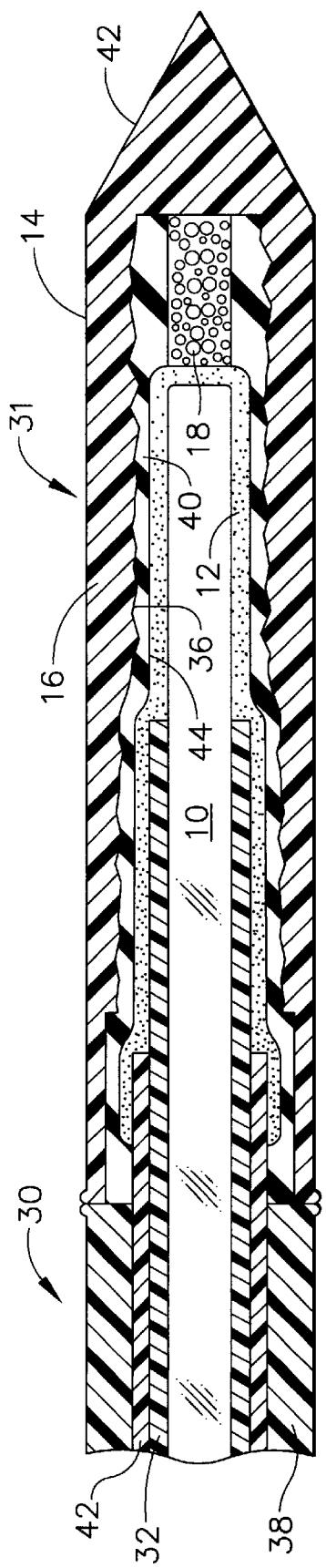
FIG. 3 is a section view of an embodiment of the diffuser tip assembly according to the present invention showing, from inside to the surface, a core, a protective coating, an optical coupling layer, and a sleeve.

FIG. 2 illustrates schematically a medical instrument 20 for diffusing light from an optical fiber. The medical instrument 20 includes a source of light energy 22, preferably a laser. An optical fiber 28 connects to the source of light energy 22 through a connection port 24 through to the diffuser tip 14. The diffuser tip 14 is affixed at the distal portion 31 of the optical fiber 28 creating the diffuser tip assembly 34. FIG. 3 shows that proximal to the diffuser tip 14, a core 10 radially surrounded by cladding 32 and a jacket 38 forms the proximal portion 30 of the standard optical fiber 28. The optical fiber 28 may also have a buffer layer 42 placed circumferentially between the cladding 32 and the jacket 38. The material used to create the cladding 32 has an index of refraction lower than the index of refraction of the material used to create the core 10.

FIG. 3 is a section view of one embodiment of the diffuser tip assembly 34 according to the present invention. In the embodiment illustrated in FIG. 3, a protective coating 12 surrounds the unclad core 10 at the distal portion 31 of the optical fiber 28. A material having an index of refraction between the indices of refraction of the core 10 and the optical coupling layer 40 forms the protective coating 12. Polymethyl methacrylate, commonly called acrylic, can be used to form the protective coating 12 when the core 10 is made from silica glass. In a further embodiment, methylpentene can be used to form the protective coating 12 when the core is made from silica glass. Silica glass has an index of refraction of 1.45 and polymethyl methacrylate has an index of refraction of 1.488. TPX™ brand of methylpentene, available from Mitsui Petrochemical Industries, Ltd. in Tokyo, Japan, has an index of refraction of 1.463. An optical coupling layer 40 surrounds the protective coating 12. General Electric XE5844 Silicone, having an index of refraction of 1.51, can be used to form the optical coupling layer 40. Proximal of the distal end of diffuser tip 14, the protective coating 12 surrounds the portion of the core 10 that has cladding 32 remaining on it but has had the jacket 38 removed.

In the embodiment of the invention, the material properties used in the protective coating 12 cause the desirable qualities. The material used in the protective coating 12 has an index of refraction between that of the core 10 and the optical coupling layer 40. The protective coating 12 also increases the ability of the optical fiber to withstand bending without breaking.

The sleeve 16 surrounds the optical coupling layer 12. The sleeve 16 may be comprised of perfluoroalkoxy containing 10% barium sulfate and has an index of refraction lower than the index of refraction of the optical coupling layer 40. Because the index of refraction decreases across the interface 36 of the optical coupling layer 40 and sleeve 16 as light moves from the optical coupling layer 40 to the sleeve 16, the interface 36 between the sleeve 16 and the optical coupling layer 40 is roughened, or abraded, to allow light to diffuse through the interface 36. This abrasion can take place on the inner surface of the sleeve 16. The abrasion can vary along the axial length of the diffuser tip 14. Varying the roughness allows the diffuser tip 14 to distribute light in a manner advantageous for the application.

A slug 18 can be placed at the end of core 10 to reflect light. The slug 18 can be comprised of alexandrite particles mixed into UV-10 Medical adhesive and cured in place. The same outer dimension as the core 10 or a smaller dimension can serve as the outer boundary of the slug 18. UV-10 Medical adhesive is available from Master Bond, Inc., Hackensack, N.J.

FIGS. 2 and 3 illustrate components that direct the light. Light travels from the source of light energy 22 through the connection port 24 and out through the core 10 of the optical fiber 28. The light proceeds through the core 10 of the optical fiber 28 without leaking through the cladding 32 because of the lower index of refraction in the cladding 32. The light then moves to the portion of the core 10 in the interior of the diffuser tip 14. Light emerges from the optical fiber 28 to the diffuser tip 14 where the protective coating 12 has an index of refraction higher than the index of refraction of the core 10. The higher index of refraction of the protective coating 12 pulls the light out of the core 10. The light then moves to the optical coupling layer 40, through the interface 44 between the optical coupling layer 40 and the protective coating 12, pulled from the protective layer 12 by the higher index of refraction of the optical coupling layer 40.

A lower index of refraction in the sleeve 16 than in the optical coupling layer 40 necessitates a roughened surface between them. The roughened, or abraded, nature of the inner surface of the sleeve 16 presents small surface portions that alter the normal trajectory of the light rays. Light rays, now altered in direction, approach the sleeve 16 at a more nearly normal angle allowing them to escape. Varying the roughness along the axial length of the abraded surface varies the intensity of the light as a function of the axial distance along the diffuser tip 14.

An alexandrite filled slug 18 placed distally to the core 10 causes light reaching the end of the core to scatter back through the core 10. Backscatter of light at the distal end of the diffuser tip 14 raises the intensity of the light nearer the distal end of the diffuser tip 14.

Scattering materials other than alexandrite can fill the slug 18, for example, aluminum oxide, titanium dioxide, or diamond powder. Alexandrite, however, fluoresces in a temperature-dependent manner detectable in ways known in the art.

Performing a simple experiment compares the bending moments tolerated by a bare core 10 and the core 10 coated with the protective coating 12. Test the moments using a section of bare core 10 and another section of core 10 with only the protective coating 12 retained on it. Strip the jacket 38, the buffer layer 42, and the cladding 32 from a length of optical fiber 28. Restrain the created length of bare core 10 in a test fixture. Place a measured force perpendicular to the axis of the bare core 10 at a known distance from the restraint point. Increase the force until the bare core 10 breaks. Multiply the force at which the core 10 breaks by the distance from the restraint point to obtain the bending moment at failure. Repeat this test for a length of core 10 coated with only protective coating 12. The proper protective coating 12 raises the bending moment at failure of the core 10. A more durable diffuser tip results.

A diffuser tip 14 can be created by using this process. Strip the jacket 38 and the cladding 32 from the optical fiber 28. Leave the bare core 10 covered with the cladding 32 exposed for a distance and the bare core 10 itself exposed for a distance further. Dip the exposed portions a number of times into a substance such as an acrylic monomer solution until the thickness of the protective coating 12 reaches the desired level. The acrylic monomer solution can be, for example, 35% by weight of acrylic monomer dissolved in 65% by weight of methylene trichloroethylene. Allow the acrylic to dry. Close a piece of the sleeve material at one end, fill the created sleeve 16 with the liquid material for the optical coupling layer, then slide the sleeve 16 onto the hardened acrylic polymer. Heat stake into position. Using a hot mold closes the sleeve 16 and may, if desired, produce a pointed tip 42. The inner surface of the sleeve 16 may be roughened with a tool, for example, a small brush.

The technician can alternatively place the molded slug 18 into the sleeve before assembling it to the coated core. To add the molded slug 18, place the molded slug 18 filled with a light scattering material into the sleeve 16. Follow by placing the sleeve 16 over the protective coating 12. A material such as silicone may form the slug 16.

The optical coupling layer 40, in addition to coupling light from the protective layer 12, helps hold the sleeve to the protective coating 12. The adhesive properties of the optical coupling layer 40 help when coiling the optical fiber 28. The coiling pulls the core 10 of the optical fiber 28 through the jacket 38 causing a relative motion between the core 10 and the jacket 38 known as "pistoning." The adhesive properties prevent pistoning and keep the core 10 and its protective coating 12 in the sleeve.

It will be recognized that equivalent structures may be substituted for the structures illustrated and described herein and that the described embodiment of the invention is not the only structure which may be employed to implement the claimed invention. For example, the pattern of roughening may distribute the light in an uneven manner advantageous to the application.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A medical instrument, said medical instrument comprising:
   an optical fiber wherein said optical fiber comprises:
      a core having a first index of refraction and a first bending moment at failure;
      a proximal portion including a cladding layer surrounding said core;
      a distal portion comprising an unclad core;
      a diffuser tip affixed to said optical fiber at said distal portion thereof, said diffuser tip comprising:
         a polymethyl methacrylate coating radially surrounding said distal portion of said optical fiber wherein said polymethyl methacrylate coating has a second index of refraction which is greater than said first index of refraction, said distal portion of said optical fiber including said polymethyl methacrylate coating wherein said core including said polymethyl methacrylate coating has a second bending moment at failure greater than said first bending moment at failure;
         an optical coupling layer radially surrounding at least a portion of said polymethyl methacrylate coating wherein said optical coupling layer has a third index of refraction greater than said second index of refraction; and
         a sleeve radially surrounding at least a portion of said optical coupling layer.

2. A medical instrument according to claim 1 wherein said optical coupling layer comprises silicone.

3. A medical instrument according to claim 1 wherein said sleeve further comprises an abraded inner surface.

4. A medical instrument according to claim 1 further comprising a slug affixed to the distal end of the core, said slug containing alexandrite particles.

5. A medical instrument, said medical instrument comprising:
   an optical fiber wherein said optical fiber comprises:
      a core having a first index of refraction and a first bending moment at failure;
      a proximal portion including a cladding layer surrounding said core;
      a distal portion comprising an unclad core;
      a diffuser tip affixed to said optical fiber at said distal portion thereof, said diffuser tip comprising:
         a methylpentene coating radially surrounding said distal portion of said optical fiber wherein said methylpentene coating has a second index of refraction which is greater than said first index of refraction, said distal portion of said optical fiber including said methylpentene coating wherein said core including said methylpentene coating has a second bending moment at failure greater than said first bending moment at failure;
         an optical coupling layer radially surrounding at least a portion of said methylpentene coating wherein said optical coupling layer has a third index of refraction greater than said second index of refraction; and
         a sleeve radially surrounding at least a portion of said optical coupling layer.

6. A medical instrument according to claims 5 wherein said optical coupling layer comprises silicone.

7. A medical instrument according to claim 5 wherein said sleeve further comprises an abraded inner surface.

8. A medical instrument according to claim 5 further comprising a slug affixed to the distal end of the core, said slug containing alexandrite particles.

* * * * *